United States Patent [19]

Krueger

[11] 4,330,437

[45] May 18, 1982

[54] SUPPORTED SILVER CATALYST AND A PROCESS OF PREPARING IT

[75] Inventor: Bruno O. Krueger, Springfield, Oreg.

[73] Assignee: Borden, Inc., Columbus, Ohio

[21] Appl. No.: 204,153

[22] Filed: Nov. 5, 1980

[51] Int. Cl.³ .............................................. B01J 23/50
[52] U.S. Cl. ..................................... 252/476; 568/473
[58] Field of Search ................. 252/463, 476; 568/473

[56] References Cited

U.S. PATENT DOCUMENTS

| | | | |
|---|---|---|---|
| 3,258,433 | 6/1966 | Lambert et al. ..................... | 252/463 |
| 3,775,346 | 11/1973 | Calcagno et al. ................ | 252/476 X |
| 3,956,184 | 5/1976 | Kruglikov et al. ............. | 252/476 X |
| 3,962,136 | 6/1976 | Nielsen et al. .................... | 252/476 X |
| 4,087,383 | 5/1978 | Gernand et al. ................ | 252/476 X |

FOREIGN PATENT DOCUMENTS 593713  3/1960  Canada ............................... 252/476

*Primary Examiner*—W. J. Shine

*Attorney, Agent, or Firm*—George P. Maskas; Kenneth P. Van Wyck; Daniel D. Mast

[57] ABSTRACT

A process for preparing a granular, supported silver catalyst by: contacting refractory porous granules having a tap volume of about 1 to 2 grams per cubic centimeter with water or a water soluble liquid having a boiling point of less than about 105° C. so as to wet said granules and to absorb water or said soluble liquid within peripheral pores of said granules; contacting the wet granules with an ammoniated solution containing a silver salt which decomposes on calcination at a temperature below about 600° C. and a fatty acid having from about 12 to 22 carbon atoms, the quantity of silver salt in said solution being sufficient to provide a metallic silver deposit onto said granules of from about 1 to 10% by weight of said dry granules; drying the silver solution on the granules, and heating the dried granules at a temperature sufficient to decompose the dried silver compounds to metallic silver. The catalyst is particularly advantageous for the manufacture of formaldehyde in place of the use of silver crystals.

11 Claims, No Drawings

SUPPORTED SILVER CATALYST AND A PROCESS OF PREPARING IT

BACKGROUND OF THE INVENTION

1. Field of the Invention

This invention relates to new and useful improvements in supported silver catalysts, their method of preparation and use, particularly, in the manufacture of aldehydes such as formaldehyde.

2. The Prior Art

The use of silver as a catalyst for many different types of reactions is well known. Silver used in catalytic reactions can be in the form of solid silver crystals or the silver can be coated on to an inert substrate to produce a supported silver catalyst. Generally, such supported silver catalysts are on porous refractory spheres, rings, pellets and the like. Supported silver catalysts find application in a number of chemical reactions such as hydrogenation, cracking, dehydrogenation and the production of ketones and aldehydes from primary and secondary alcohols. Silver is an expensive material and a variety of techniques have been developed for depositing relatively small amounts of silver on refractory material and the use of such silvered material in place of solid silver.

U.S. Pat. No. 3,956,184 of May 11, 1976 to Kruglikov, et al., and U.S. Pat. No. 4,126,582 of Nov. 21, 1978 to Diem, et al., describe preparation of supported silver catalysts for use in the manufacture of formaldehyde. The supported silver catalysts of those patents suffer from a number of shortcomings, particularly their method of manufacture which relies on the use of strong chemical reducing agents. I find that the use of the reducing agent techniques of these two patents is not practical because of the large quantities of solutions required in the silver deposition techniques which also coat the equipment with silver. There is a residual silver powder suspension in the solution to be filtered out and the residual strongly alkaline solution containing toxic reducing agents has to be disposed. Much the same problem exists with the extensive washing needed and disposal of the contaminated wash water. The silver on the equipment has to be removed prior to the next batch or the silver will preferentially deposit on the existing silver surface. If promotors are to be added to the supported catalyst in order to optimize the reaction equilibrium, the reduction methods of these two patents are not suitable for homogeneous distribution of the promoter metal unless a compound of the promoter is used which reduces under the same conditions as the silver. Also, particularly in the case of 184 patent, the silver would penetrate deep into the carrier and thus much of the silver would not be available for the catalytic reaction.

U.S. Pat. No. 2,462,413 mentions the use of a supported silver catalyst for the preparation of formaldehyde. The catalyst is placed, as a bed, in insulated silica tubes wherein from about 0.5 to about 10% of silver is deposited on the carrier such as pumice or alumina-silica refractories. This patent does not describe: preparation of the support prior to silver deposition; how the silver is deposited on the support; and little information is given as to other properties of the silver coated support.

U.S. Pat. No. 3,702,259 prepares supported silver catalysts by use of oranic amine solubilizing and reducing agents for depositing silver on porous refractory supports. The catalyst preparation methods of this invention as well as the catalyst itself, suffer from much the same shortcomings as the before mentioned methods, e.g., use of toxic reducing agents and loss of silver by penetration into the porous carrier. Although the principal utility of the catalyst of this 259 patent is for the manufacture of ethylene oxide, the patent does mention utility for a variety of chemical reactions, including the preparation of aldehydes from primary alcohols.

U.S. Pat. No. 2,805,229 shows the preparation of supported silver on porous refractory tubes. The silver is deposited on the tube surfaces from an ammoniated silver solution which is subsequently dried on the tubular carrier and then heated at about 250° C. to 350° C. to decompose the silver compounds to metallic silver. It appears that both the inside and outside surfaces of the tubes are coated with silver and the silver penetrates into the porous carrier. The tubular catalysts of this patent are described as useful for the oxidation of ethylene to ethylene oxide.

U.S. Pat. No. 3,725,302 of Apr. 3, 1973 to Brown, et al., shows the preparation of supported silver catalyst for the production of ethylene oxide. This patent mentions the use of spherical supports wherein the silver is deposited throughout the pores of the particle by immersing the support in an aqueous solution of a silver salt, drying the support and finally heating the support at a temperature sufficient to decompose the silver salt. Optionally, an alkaline earth promoter is added to the silver salt solution.

U.S. Pat. No. 3,981,825 of Sept. 21, 1976 to W. J. Raegan shows metallic reforming catalysts prepared by mixing a solid porous support with a solution of various soluble metal compounds in dimethylsulfoxide, subjecting the resulting slurry to refluxing, separating the solid carrier from the slurry, drying the carrier and finally calcining the metal compound impregnated carrier.

U.S. Pat. No. 2,424,083 describes the preparation of supported silver catalysts together with promoter metals wherein the silver solution is contacted with the support and reducing agents convert the metal salts to a metallic coating on the support or carrier.

U.S. Pat. No. 2,765,283 of Oct. 2, 1956 to Sacken shows the preparation of supported silver catalysts wherein the support is first washed with a chlorine solution to deposit small quantities of chlorine compound on the support. Following a wash of the chlorine containing support, the carrier particles may be dried. The support is then contacted with silver oxide, such as silver oxide paste and then dried, and finally the silver oxide is reduced to metallic silver.

U.S. Pat. No. 1,067,665 of July 15, 1913 describes preparation of silver catalysts by precipitating a silver salt from an ammoniated solution, applying the salt to various supports and apparently finally calcining the salt on the support. Prior to contact with the silver salt, the support is also calcined to rid it of organic matter.

SUMMARY OF THE INVENTION

Silver catalyst is prepared by contacting an inert porous carrier with a volatile liquid so as to wet said carrier, coating the wet carrier with an ammoniated solution of a silver salt, drying the coating on to said carrier and finally calcining such coated carrier at a temperature sufficient to obtain a metallic silver coating thereon. In preferred embodiments, the solution of silver salt contains sufficient silver to deposit from about 1% to 10% and more preferably from about 2% to 8% of silver, based on the weight of a granular support having a particle size of about 0.2 to about 2.5 millimeters. The silver salt solution also contains minor quantities of a fatty acid having from about 12 to 22 carbon atoms. The supported silver catalyst is particularly useful for the manufacture of formaldehyde from methanol and oxygen gas e.g., with air, in a fixed bed wherein the supported catalyst is used in place of conventional solid silver crystals.

DETAILED DESCRIPTION OF THE INVENTION

The silver salt solution employed in the manufacture of the catalyst contains: (a) a silver salt; (b) ammonia; and (c) an aqueous solvent.

Suitable silver salts include: organic or inorganic salts of silver, particularly those which decompose when calcined at temperatures below about 600° C., and preferably not higher than about 500° C. to give metallic silver. Illustrative of inorganic silver salts there can be mentioned the nitrate, nitrite, and carbonate. Silver oxide is also suitable and since it forms salts or complexes with the ammonia, the term "salt" as used herein includes silver oxide. Illustrative of organic acid salts there can be mentioned the silver salts of carboxylic acids such as those of mono-, di- and tribasic aliphatic and aromatic carboxylic and hydroxycarboxylic acids such as those having of 1 to 8 carbon atoms. Examples of such acid salts of silver are the carbonate formate, acetate, propionate, oxalate, malonate, phthalate succinate, lactate, tartrate, citrate, and the like.

Ammonia aids in the solubilization of the silver and forms water soluble complexes with difficulty soluble silver salts. The solvent employed in the silver salt solution is water. Other materials such as lower alkanols having from 1 to about 4 carbon atoms or ketones may be added in minor quantities to the washer to aid solubilization of the silver salt. The ammonia can be provided as aqueous ammonia, ammonium hydroxide and the like. The quantity of ammonia employed is that sufficient to maintain a stable solution of the silver salt and other additives; however, an excess of such amount is not deleterious.

The concentration of silver salt in the solution can be in the range of from about 0.1% by weight to the maximum permitted by the solubility of the salt solution, containing ammonia and optionally organic solvent such as the alcohols. The concentration of the salt in solution and total quantity of solution to be used is preferably adjusted so that the quantity of silver therein is equal to the desired quantity of silver coating on to the support.

The surface of the wet support to be coated with silver can be first covered by the silver salt solution by conventional procedures, e.g., spraying, dipping, soaking, and the like procedures are suitable. It should be recognized that the silver salt solution contains various complexes of silver, some of which may be silver oxide complexes which are solubilized by the ammonia.

The silver salt solution of the invention will preferably also contain a fatty acid having from about 12 to 22 carbon atoms. The fatty acid can be saturated or vinyl unsaturated. The quantity of fatty acid, or ammonium salt thereof can vary over a broad range such as that of from about 0.1% to 10% by weight of the silver salt solution used to coat the carrier. Preferably the quantity of such acid or ammonium salt, thereof, is from about 0.5% to 5% of the silver salt solution. Since the silver salt solution is ammoniacal, the fatty acid will form the ammonium salt, thereof, in such ammoniacal solution. Illustrative of suitable fatty acids there can be mentioned: oleic acid, linoleic acid, stearic acid, palmitic acid, behenic acid, palmitic acid, myristic acid, lauric acid, and the like. The use of these fatty acids in the invention aids in the formation of uniform, smooth adherent silver coatings of silver on the substrate.

The support can be selected from the large number of conventional porous refractory catalyst carriers or support material. The support material can be in various shapes such as particles, chunks, pieces, pellets, rings, rods, spheres and the like, particularly those of a size suitable for employment in fixed bed applications. Suitable supports comprise those of siliceous and or aluminous compositions. Specific examples of suitable supports are porous aluminum oxides, including materials sold under the trade name "Alundum." Also, pumice, magnesia, kieselguhr, fullers earth, silicon carbide, porous agglomerates comprising silicon and or silicon carbide, selected clays, oxides of heavy metals such as chromium, molybdenum, ceramics, alpha-alumina, alumina-silica refractory, etc. The size of the support can vary over a wide range. Thus in coating silver on to reaction tubes, the tubes can be two or more feet long and an inch or more in inside diameter. However, the catalyst support is preferably granular with particule sizes from about 0.1 to 5 millimeters.

Preferably, the support is in the shape of rod or "spaghetti" shaped refractory particles having a thickness of about 0.4 to 0.6 millimeters, and a length of about 0.5 to 2.0 millimeters (mm). This shape of support is preferred since it resembles the shape of the silver crystals normally used in the manufacture of formaldehyde.

The porous support materials preferably have a tap volume of from about 1.0 to 2.0 grams per cubic centimeter. For the manufacture of formaldehyde, the tap volume is preferably from about 1.3 to 1.8 grams per cubic centimeter and particularly about 1.5 grams per cubic centimeter. We found that such support (Kellundite) having a tap density of 1.3 grams per cubic centimeter had a water absorption of 20% while a support with a tap density of 1.5 grams per cubic centimeter had a water absorption of 18% by weight based on the dry support.

In a preferred embodiment for the manufacture of the catalyst, the silver salt solution is added to the wetted support in a rotary dryer wherein preheated air is passed over the tumbling mass of support particles at a temperature sufficient to dry the silver salt coated support, e.g., at a temperature of about 70° C. to about 105° C., and preferable about 80° C. to 100° C., until a dry granular coated support is obtained. Due to the pre-wetting, the support pores have been filled with water or another volatile liquid, i.e., which boils at a temperature of about 105° C. or less. The pre-wetting and coating with the silver solution while the support is wet with volatile liquid prevents deep penetration of the added silver solution. Apart from the volatile liquid finding its way into the pores of the support, evaporation of the volatile liquid from within the porous support, keeps the silver salt on the support surface until dry. The dried catalyst is then subjected to temperatures sufficient to decompose the dried silver salt. Such temperature can vary from about 300° C. to 700° C. Preferably, the dried support is calcinied in a kiln wherein the temperature varies from about 500° C. to 600° C. for about 1 to 3 hours to decompose the dried silver salts to form a uniform layer of the silver together with any promoters which may have been added. For commercial production on a continuous basis the support can be wetted at the entry of a rotary drier and the silver solution can be metered further down into the moving, wet mass for homogeneous distribution. As the tumbling mass moves toward the outlet of the rotary dryer against a countercurrent stream of hot air, the dried and coated support will be discharged, ready for pyrolytic decomposition. An advantage in the use of a rotary drier is that substantially all of the solids in the silver solution are coated on to the porous carrier.

The spent catalyst of this invention can be recovered for recycle both as to the silver and the support material. The spent catalyst is removed from the reactor or burner and extracted with nitric acid to obtain a silver nitrate solution for reuse in making catalyst of this invention. The extracted support material is then heated at a temperature sufficient to burn off carbonaceous deposits such as those which form in the manufacture of formaldehyde. Such temperature is preferably from about 600° C. to 700° C. The support is then ready for repeated coating with silver from the earlier extraction. This procedure can be repeated many times for the recycling of spent catalyst and manufacture of catalyst of this invention.

The following Tests and Examples are illustrative of the invention:

Testing of the supported catalyst preparation of the invention was made in a multiple reactor plant, operating with a silver crystal catalyst in the production of formaldehyde from methanol and oxygen gas, e.g., air. Four of 64 reactors in total, operating in parallel, were used for the testing. The feed flow rates were adjusted to the same velocity as for the silver crystal reactors by measuring and adjusting feed velocity based on Pitot Tube readings. Each reactor was equipped with sample valves at its outlet into the main header and temperature measurements were made directly under each catalyst bed by thermocouple. This was necessary in order to make a valid comparison with the silver crystals for which the air methanol ratio was adjusted. The burners had a diameter of 8 inches. About 1 inch layer of silver crystals or catalyst of this invention were used in each burner wherein the catalyst was supported on a copper screen of about 80 mesh.

Concerning the solid ceramic support, the uncoated support materials were first tested for inertness by placing them under a regular silver crystal catalyst layer which was operated normally in one of the test reactors. After 24 hours of operation, gas and condensate samples were taken from the test burner and results of analysis compared with the total plant operation. The support was considered as inert if no deviation of compositions had occurred. The finally selected inert support was a ceramic composition produced by the Filtros Division of the Ferro Corporation, sold as "Kellundite" catalyst support. Several types of this support were found satisfactory ranging in tap volumes from 1.3 gram per cubic centimeter to 2.0 gram per cubic centimeter. I prefer to use the medium porosity material with a tap density of 1.5 cubic centimeter per gram.

The silver salts solutions used for support coating were usually prepared from fresh silver nitrate or silver nitrate solutions obtained from extraction of spent catalyst.

For the following examples, aqueous ammonia of about 25% concentration was slowly added to the silver nitrate solution in such a quantity that an initial precipitation of silver hydroxide clearly dissolved as a complex, further additions were made to this complex solution as set forth in the examples.

The term "mesh" as used herein refers to Tyler Screen sieves.

EXAMPLE 1

1,500 grams of Kellundite support in form of "spaghetti" at −20 to +40 mesh with a tap density of 1.5 gram per cubic centimeter was wetted with 300 ml of water. This had a particle size of about 0.4 to 0.6 millimeters in diameter about 0.5 to 2.0 millimeters long. To the wetted support, the following solution was added which had been prepared in the following order: 200 ml water; 24 grams of silver nitrate; 200 ml 25% ammonia; and 12 grams of ammonium stearate.

The mixture was dried in a rotary dryer wherein substantially all of the silver solution was coated on to the support material. The silver salts on the dried support were decomposed at about 500° C. in a gas fired kiln. Natural gas was used as fuel in the kiln but I prefer to use the hydrogen containing "Tailgas" from the formaldehyde plant for increased reduction potential and freedom of sulfur compounds.

850 ml of this catalyst was placed in a previously described test burner, representing about 1 inch thick layer of catalyst bed. The reaction was started by introduction of reactor feed gas as it was used in the other burners, operating with silver crystals. Reaction temperatures were in excess of the silver crystal operation and the conversion of methanol to formaldehyde was lower than in the rest of the plant. The test was terminated since the silver content of the catalyst amounted to only about 1% and did not seem to be adequate for economical operation.

EXAMPLE 2

1,500 gram of catalyst support as in Example 1 were wetted with 400 ml (millileters) methanol. A solution prepared from the following ingredients was added to the wetted support in a rotary dryer: 300 ml of water; 71 grams of silver nitrate; 200 ml 25% ammonia solution; and 12 grams of ammonium stearate.

The solution of silver on the carrier was dried in a rotary dryer at 80°–90° C. by a preheated stream of air. Substantially, all of the silver solution was coated on the catalyst support. The dried catalyst mass was heated to about 500° C. for about 1 hour, resulting in a supported silver catalyst with a shining silver layer of 3% by weight, which had little or slight penetration into the surface of the porous support. 850 ml of the prepared catalyst were placed in the test reactor and put into service. This catalyst operated for 44 days comparable to the silver crystals with respect to reaction temperature, methanol conversion and efficiency. It sustained during this time 10 start ups, including on where the silver crystals in the plant had sintered by a high temperature runaway and had to be replaced.

EXAMPLE 3

1,500 gram "Kellundite" support having substantially the same physical properties as that used in Example 1 were wetted with 300 ml of water and then a solution of the following ingredients was added to the wet support:

119 grams of silver nitrate; 200 ml water; 200 ml ammonia 25%; and 12 grams of ammonium stearate.

The support coated with substantially all of the solids of the silver solution was dried at about 80°-90° C. in a preheated air stream. The dried catalyst mass was heated in a kiln to 500° C. for one hour. A supported catalyst resulted with a shining silver surface of about 5% by weight, silver which had only little penetrated into the partially porous support. About 850 millileters of this catalyst were placed in a test burner and put into operation. The temperatures obtained were comparable with silver crystals, but the conversion of methanol to formaldehyde was about 6-7% higher using the supported catalyst of this Example.

EXAMPLE 4

1,500 grams "Kellundite" support were wetted with 400 ml of methanol. To the wetted support, in a rotary dryer, the following solution was added: (A) 300 ml water, containing 95 grams silver nitrate; and (B) 200 ml 25% ammonia solution, containing 10 grams oleic acid as ammonium-oleate in solution.

The above items A and B were mixed before addition to the rotary dryer and the mass dried at 80°-90° C. The dried catalyst was heated to between 400°-600° C. for one hour, resulting in a catalyst with about 4% weight of shiny silver on the surface.

EXAMPLE 5

1,500 grams of porous catalyst support were wetted with 300 ml water in rotary dryer. The support was a refractory material having a tap volume of about 1 to 2 grams per cubic centimeter, and a particle size of from about 0.1 to 5 mm. To the wetted support, the following mix was added.
(A) 119 grams silver nitrate, containing about 75 grams silver metal and 17 grams zinc nitrate, containing about 3.7 grams zinc metal. Both were dissolved in 300 ml water.
(B) 200 ml 25% ammonia solution, containing 20 grams ammonium stearate.

The above A and B solutions were mixed and added to the wetted support in the rotary dryer for drying at 80°-90° C. The dry mass was heated to about 500° C. for two hours to decompose the dried silver and zinc nitrate ammonia complex. There was a shiny layer of about 5% silver on the support surface which also contained 0.25% zinc as metal or metal oxide (based on the dry support).

Unless the porous supports are pre-wetted, the silver forms within the catalyst particles and it requires much more silver than merely forming an adherent coating on the surfaces of the catalyst support.

By pre-wetting the support with a volatile liquid, penetration of silver is minimized. The dried and heated support of the Examples did not show more than about 10-15% silver penetration into the body of the support while 85-95% of the particle showed no silver deposited. These percentages are based on the thickness of the support. Thus, deposition of silver on the outer layer of catalyst particle and such deposition extending into the core by 0.1 mm in a 1 mm thick particle would be a 10% penetration. By using this method, the volatile liquid of pre-wetting prevented the silver complex solution from entering into the semi-porous support. Furthermore, during the drying step, the volatile liquid from the interior of the support had to move outward and carry the silver complex solution toward the surface.

PLANT AND TEST OPERATING CONDITIONS FOR THE FORMALDEHYDE PRODUCTION IN THE EXAMPLES

The average feed composition to the reactor at about 80° C. was as follows:

| Methanol | Mol. % | 45.64 |
|---|---|---|
| Oxygen | Mol. % | 11.41 |
| Nitrogen | Mol. % | 42.95 |

The reactor outlet composition at 450°-600° C. consisted of an average concentration of Mol.% as below:

| Methanol | 11.36 |
|---|---|
| Formaldehyde | 23.59 |
| Water | 13.26 |
| Hydrogen | 13.26 |
| Nitrogen | 35.63 |
| By-Products | 2.90 |

Gas analysis of the rest gas, the not condensables of the process, were made for comparison between the supported catalyst and the regular silver crystal catalyst. A typical example is as follows:

|  | Plant on Silver Catalyst | Supported Catalyst |
|---|---|---|
| Carbon Dioxide | 4.6% (Vol) | 3.0% |
| Hydrogen | 23.9 | 20.4 |
| Carbon Monoxide | 0.4 | 0.2 |

In using an ammonia complex of silver salt and the fatty acid or ammonia salt thereof, there is formed salts or complexes of the fatty acid and silver. This provides an eutectic mixture of salts during the process of drying in the rotary dryer. This mixture does not have the tendency of crystallizing, but rather forms a uniform coating of a homogeneous layer of both salts. During the subsequent heating, this mixture melts to flow evenly over the support surface. Furthermore, when this mixture decomposes during the heating, the fatty acid carbonizes and aids in the reduction of the silver to the metal.

The "Kellundite" used as a support carrier in this application is a refractory calcined mixture containing on a percent by weight basis: aluminum oxide 74.96 to 84.71%; silicon dioxide 20.99 to 10.83%; sodium oxide 0.75 to 1.64%; patassium oxide 0.19 to 0.67%; calcium oxide 0.33 to 1.34%; magnesium oxide 0.81 to 1.81%; ferric oxide 0.15 to 0.24% and titanium dioxide 0.21 to 0.36%.

What is claimed is:
1. A process of preparing a supported silver catalyst which comprises:
(a) contacting an inert porous carrier with water to wet the surface of said carrier;
(b) contacting the wet carrier with an ammoniated aqueous solution of a silver salt;
(c) drying the silver solution on the carrier; and
(d) heating the dried carrier at a temperature sufficient to decompose silver compounds on the carrier to metallic silver.
2. A process of claim 1 wherein the ammoniated silver solution contains from about 0.5% to 5% of an aliphatic fatty acid having from about 12 to 22 carbon atoms.

3. A process of claim 1 wherein the size of the inert carrier varies from about −20 to +40 mesh.

4. A process of claim 1 wherein the carrier is in the shape of rods having a diameter of about 0.4 mm to 0.6 mm and lengths of about 0.5 mm to 2 mm.

5. A process of claim 4 wherein the carrier has a tap volume of about 1.3 to 1.8 grams per cubic centimeter.

6. The process of claim 1 wherein the silver salt is silver nitrate.

7. A process for the production of granular, supported silver catalyst which comprises:
    (a) passing an inert granular porous carrier which has been wetted with water through a rotary dryer;
    (b) contacting the wet carrier with an aqueous solution of a silver salt as it moves through said dryer to form a coating of said solution on said carrier;
    (c) drying said coated carrier as it moves through said dryer; and
    (d) placing said dry carrier in a kiln at a temperature sufficient to decompose silver compounds on the dried carrier to metallic silver.

8. A porous inert carrier having a particle size from about 0.2 to about 2.5 millimeters and a tap volume of about 1.3 to 1.8 grams per cubic centimeter coated with metallic silver in a quantity of from about 1% to 10% by weight of the carrier, said silver being adherent to the periphery of said carrier, the penetration of the silver within said carrier being no greater than about 15% of the thickness of said carrier.

9. A method for preparation and recycling of supported silver catalyst for the manufacture of formaldehyde from methanol and oxygen at elevated temperatures which comprises:
    (a) contacting an inert porous carrier with water so as to cause wetting of the carrier, said carrier being a refractory material having a width of about 0.4 to 0.6 millimeters and a length of from about 0.5 to 2 millimeters and having a tap volume of from about 1.3 to 1.8 grams per centimeter;
    (b) contacting the wetted carrier in a rotary dryer with an ammoniated solution of silver nitrate in an amount sufficient to coat said carrier with from about 2 to 8% of its dry weight with metallic silver, said solution also containing a fatty acid having from about 12 to 22 carbon atoms;
    (c) drying said solution as a coating on the carrier by countercurrent passage of hot air through said rotary dryer;
    (d) heating said coated and dried carrier at a temperature sufficient to decompose the silver compound deposited on said carrier to metallic silver;
    (e) placing said silver coated carrier in a reactor wherein formaldehyde is produced at elevated temperatures from methanol and air in the presence of said silver coated carrier catalyst until said catalyst is spent;
    (f) removing said catalyst from the reactor and extracting the silver from the support with nitric acid to obtain silver nitrate;
    (g) then heating the support at a temperature of from about 600° C. to 700° C. to burn off carbon developed in use of the catalyst; and
    (h) repeating the above steps (a) through (g) in the order set forth above.

10. A process for preparing a granular, supported silver catalyst which comprises:
    (a) contacting refractory porous granules having a tap volume of about 1 to 2 grams per cubic centimeter with water, so as to wet granules and to absorb water within peripheral pores of said granules;
    (b) contacting the wet granules with an ammoniated solution containing a silver salt, which decomposes on calcination at a temperature below about 600° C. and a fatty acid having from about 12 to 22 carbon atoms, the quantity of silver salt in said solution being sufficient to provide a metallic silver deposit on to said granules of from about 1 to 10% weight of said dry granules;
    (c) drying the silver solution on the granules; and
    (d) heating the dried granules at a temperature sufficient to decompose the dried silver compounds to metallic silver.

11. The porous inert carrier of claim 8 wherein the metallic silver is a quantity of from about 1% to 5% by weight of the carrier.

* * * * *